United States Patent [19]
Ghiatas

[11] Patent Number: 5,158,084
[45] Date of Patent: Oct. 27, 1992

[54] MODIFIED LOCALIZATION WIRE FOR EXCISIONAL BIOPSY

[75] Inventor: Abraham A. Ghiatas, San Antonio, Tex.

[73] Assignee: Board of Regents, The University of Texas System, Tex.

[21] Appl. No.: 441,113

[22] Filed: Nov. 22, 1989

[51] Int. Cl.$^5$ ............................................. A61B 5/00
[52] U.S. Cl. .................................. 128/657; 604/717; 604/164
[58] Field of Search ................... 128/653 R, 656–658, 128/653.1; 604/117, 164–169; 606/130

[56] References Cited

U.S. PATENT DOCUMENTS

| | | | |
|---|---|---|---|
| 2,091,438 | 6/1936 | Epstein | 604/117 |
| 3,016,899 | 1/1962 | Stenvall | 606/130 |
| 3,452,742 | 7/1969 | Muller | 128/657 |
| 4,509,945 | 4/1985 | Kramann et al. | 128/657 |
| 4,616,656 | 10/1986 | Nicholson et al. | 128/653 R |
| 4,655,752 | 4/1987 | Honkanen et al. | 604/167 |

OTHER PUBLICATIONS

Ranfac Corp. Brochure, "Sadowsky Breast Marking System", 1986.
Kopas, D. et al., "Spring Hookwire Breast Lesion Localizer: Use with Rigid-Compression Mammographie Systems"<Radiology, 157:537–538 (1985).
Kopans, D. et al., "A Modified Needle-Hookwire Technique to Simplify Preoperative Localization of Occult Breast Lesions", Radiology, 134-781 (1980).
Kalish, L., "An Improved Needle for Localization of Nonpalpable Breast Lesions", Radiology, 128:815–817 (1978).
Hall, F. et al., "Preoperative Localization of Nonpalpable Breast Lesions", AJR, 132:101–105 (1979).
Libshitz, H. et al., "Needle Localization of Nonpalpable Breast Lesions", Radiology, 121:557–560 (1976).
Dodd, G., "Preoperative Radiographic Localization of Nonpalpable Lesions", Detection and Treatment, edited by Gallager HS, New York, Wiley, 1975, pp. 151–152.

*Primary Examiner*—Lee S. Cohen
*Assistant Examiner*—Krista M. Pfaffle
*Attorney, Agent, or Firm*—Arnold, White & Durkee

[57] ABSTRACT

A modified wire having one or more markers for locating lesions contained within afflicted tissue, wherein the markers help establish the position of the surgeon's scalpel in relation to the tip of the wire and to the lesion so that the surgeon can quickly and accurately remove the lesion which may or may not be contained near the tip of the modified wire. Each marker comprises a palpable surface which is detectable when the surgeon encounters the marker.

4 Claims, 2 Drawing Sheets

MODIFIED LOCALIZATION WIRE FOR EXCISIONAL BIOPSY

BACKGROUND OF THE INVENTION

I. FIELD OF THE INVENTION

The invention relates to a device and a method for locating and extracting lesions. More specifically, the present invention is directed toward a modified, radiopaque wire that is placed into or near afflicted tissue. The modified wire comprises markers positioned upon the modified wire at known distances from the tip of the wire. By placing the tip of the modified wire near the lesion, the markers provide information to the surgeon as to the location of the lesion without requiring the surgeon to cut completely to the tip of the wire.

II. DESCRIPTION OF RELATED ART

Lesions are typically discovered by taking radiographs, including but not limited to X-ray photographs, of the suspect area. The radiographs confirm the general presence, size and location of one or more lesions. Once lesions are discovered, it is preferred that the lesions be extracted without having to dissect large portions of unafflicted tissue surrounding each lesion. However, a problem exists in having to translate the lesion shown on the radiograph to the exact location within the patient. Simply removing all tissue in the general vicinity proves unacceptable. If only a small lesion is discovered, it is essential that the lesion be identified and localized such that when the surgeon enters the tissue with his scalpel, he can enter the afflicted area in a direct cut without unnecessarily dissecting unafflicted tissue. Also, it is preferred that when the surgeon removes tissue, only the afflicted tissue or lesion be removed. Unafflicted tissue should remain undisturbed and intact.

In order to cut and remove lesions without disturbing unafflicted tissue, it is important that the lesion shown on the radiograph be located and identified within the actual patient before surgery. Typical localization techniques include a radiopaque wire guided into the patient's lesion area by taking a series of radiographs as the wire is being inserted. The surgeon targets the tip of the wire to be positioned as near as possible to the lesion. Often this involves taking a radiograph and then positioning the tip near the lesion. A second radiograph is often needed so that the tip can be repositioned nearer the lesion. The process is repeated, often requiring several radiographs, in order to place the tip as near the lesion as possible. Once the tip of the wire is satisfactorily positioned near the lesion, the tip of the wire is designed to remain secure inside the patient. A hook made by a bend at the tip of the wire attaches to surrounding tissue and insures that the wire will remain secure within the patient. With the wire secured in place, the surgeon can then use the wire as a guide for his scalpel. As the surgeon guides his scalpel along the wire, he knows that the lesion will reside at the end of the wire. Thus, he also knows that he must reach the tip of the wire in order the extract the lesion. However, if the lesion is not at the end of the wire, the surgeon may end up cutting or removing unafflicted tissue that resides at the end of the wire and not removing the lesion. Also, if the tip of the wire penetrates the lesion, the surgeon may unfortunately sever the lesion when hunting for the tip of the wire. Since it is preferred that the lesion be removed in whole, cutting the lesion risks removal of only a portion of the lesion.

Conventional wire localization methods requires that the surgeon cut down to the tip of the wire before he can then fix the exact location of the lesion. If the lesion resides at a remote location or a shallower location, or if the lesion is pierced by the wire tip, the surgeon may unavoidedly sever or remove unafflicted tissue while searching for the tip of the wire. In attempting to alleviate this problem, the surgeon will have to spend more time placing the wire such that the tip of the wire resides as near the lesion as possible, but not directly within the lesion. This may involve numerous radiographs to aid in repositioning of the wire. The possibility of overexposing the patient to radiation becomes a problem. Therefore, while it is desirable to place the wire tip as near the lesion as possible, numerous repositioning attempts may only create additional problems.

SUMMARY OF THE INVENTION

Accordingly, it is desirable to provide a radiopaque modified wire having radiopaque locating markers which can accurately locate lesions that reside more remotely from the tip of the wire than that enabled by conventional wires, and to provide a wire whose tip can reside within a lesion while still allowing the surgeon to remove the lesion without cutting the lesion. Most importantly, it is desirable to provide a wire that has markers placed on the wire which indicate the location of a lesion, in relation to one more markers, without requiring the surgeon to uncover the wire tip before he can fix the lesion location.

The present invention provides a modified localization wire with one or more markers placed on the modified wire, wherein each marker signifies a set distance from the tip of the wire. The modified, radiopaque wire and markers are guided into tissue of the patient according to conventional methods (i.e., using radiographs of the lesion in relation to the tip of the radiopaque wire). However, once in place, the embedded markers, placed on the modified wire, provide the surgeon with early palpable feedback as to the exact location of the lesion with respect to the marker, without requiring the surgeon to uncover the tip of the wire in order to fix the lesion location. Early palpable feedback during an incision allows the surgeon, while searching for the lesion, to modify the incision path at a shallower point, rather than having to first uncover the deeper wire tip. The markers are detectable to the surgeon's touch such that the surgeon, when making his incision along the modified wire, can ascertain the exact location of the lesion once he feels the first, second, etc. marker. When his fingers or scalpel touch the marker, the surgeon instantly knows the approximate distance to the lesion which may or may not reside at the wire tip. If the wire tip does not reside within the lesion, then the surgeon can veer his incision from the marker directly to the lesion area without having to cut deeper to the wire tip and then backtrack from the wire tip to the lesion. However, if the wire tip does reside within the lesion, the surgeon will know that he must stop his incision along the wire at a certain identified marker point on the wire so as to not cut the lesion lying at the tip of the wire. In either case, the modified wire with one or more markers proves a valuable substitute to conventional lesion localization methods.

When guiding the modified, radiopaque wire and markers into the afflicted tissue, it is not critical that the modified wire tip be placed near the lesion. However, as discussed earlier, conventional wire requires wire tip placement as near the lesion as possible, but not directly into the lesion. When placing the modified wire of the present invention, either the wire tip or the markers need be placed somewhat near the lesion but not immediately adjacent thereto. The markers add to the wire tip as being potential target points for which a nearby lesion must reside. Because there are more target points contained on the modified wire of the present invention, and because it is no longer critical that the wire tip be placed immediately adjacent the lesion, numerous radiographs and repositioning of the wire is not needed. Often, the modified wire need only be repositioned once or twice in order to place the markers or wire tip near the lesion. By minimizing the number of times the wire must be repositioned, the patient's risk of radiation exposure is also minimized.

The present invention provides a device for lesion localization comprising a wire with a collapsible hook configured at one end of the wire for insertion near said lesion area. Contained upon the wire and spaced a known distance from the collapsible hook is at least one marker. The wire is radiopaque and bent at one end thereby forming a collapsible hook. Each marker is a palpable region extending longitudinally a short distance along the wire. The spacing between each marker and between the collapsible hook and the nearest marker is substantially greater than the longitudinal length of each palpable marker region.

In a preferred embodiment, the markers comprise a radiopaque protrusion extending radially outward from the outside surface of the wire and extending longitudinally along the wire a distance much shorter than the spacing between markers or the spacing between the nearest marker and collapsible hook. The radially extending protrusions are visually detectable and detectable to the touch and can be either permanently or temporarily attached to the wire.

In another preferred embodiment, the markers comprise a textured area contained within the wire, wherein the textured area extends radially flush with the outside surface of the wire and extending longitudinally along the wire a distance substantially shorter than the spacing between markers or the spacing between the nearest marker and collapsible hook.

The present invention also provides a method for locating and extracting a lesion from afflicted tissue so that a biopsy may be performed. The method comprises the steps of inserting a needle containing a wire, having at least one marker, into the afflicted area/tissue. The end of the needle is then positioned to a point near the lesion by moving the needle according to a radiographic display. Once the end of the needle is in position, the needle is then withdrawn from the tissue leaving the wire secured within or near the lesion. With the wire in place, the surgeon can then use the wire as a guide for insertion of his scalpel into the tissue along the wire. As the incision reaches one or more markers placed at shallower locations upon the wire, the surgeon can then readjusts his scalpel in accordance with the known distance between the marker and the target lesion. Once the incision reaches the target lesion, the lesion may be extracted in whole from the surrounding unafflicted tissue.

The present invention therefore provides a modified lesion localization wire which enjoys the advantages of wire localization, while at the same time having markers for more efficient scalpel movement directly to the lesion area. Adding markers to wire also provides a modified wire of the present invention which can be quickly positioned, posing less risk of overexposing the patient to radiation. These and other advantages of the present invention will be further appreciated from the drawings and the detailed description provided below.

DETAILED DESCRIPTION OF THE INVENTION

Figure 1:
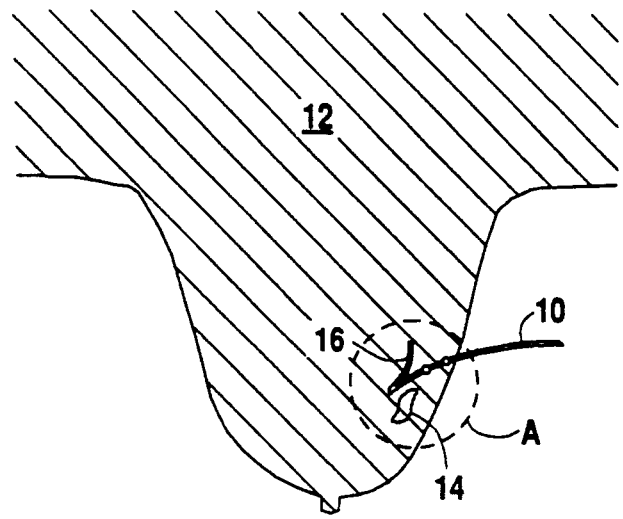
FIG. 1 is a cutaway top view of a modified localization wire of the present invention positioned in breast tissue having a lesion.

Referring to the drawings, FIG. 1 is a cutaway top view of a modified localization wire 10 embedded into breast tissue 12 containing a lesion 14. Although FIG. 1 depicts tissue 12 as being breast tissue, it is to be appreciated that modified wire 10 can be placed in any tissue for which a lesion 14, or any other type of foreign or abnormal substance, is contained. In tissue having one or more small or large lesions, it is preferred that the location of each lesion be identified. Conventional radiographic or X-ray devices (e.g., mammography devices when breast tissue is being examined) identify the general area in which a lesion exists. Once the size, shape and general location of the lesion is identified on a radiograph, the identified lesion shown on the radiograph must now be translated and localized to its exact location within the patient. The most common method of localization involves using a wire to indicate lesion location.

Conventional wire localization techniques are known in the art, and generally they involve guiding a hollow needle containing a wire into the afflicted tissue whereby the end of the needle and wire is positioned as near the lesion as possible. The hollow needle and wire are guided toward the lesion by taking a series of radiographs or mammographies of the radiopaque needle and wire which are partially embedded within the afflicted tissue region. The radiographs illustrate the lesion and its orientation with the embedded radiopaque needle. After each X-ray, the tip of the needle and wire are repositioned nearer the lesion. After several X-rays and needle repositioning movements, the tip of the needle is placed in a position near the lesion to be extracted. With the needle at the desired position, the wire is released from the needle encasement such that the tip of wire becomes secured to the tissue at the same point in which the tip of the needle resides. With the wire firmly secured in place, the needle can then be withdrawn from the tissue thereby leaving only a wire partially embedded into the tissue.

Figure 2:
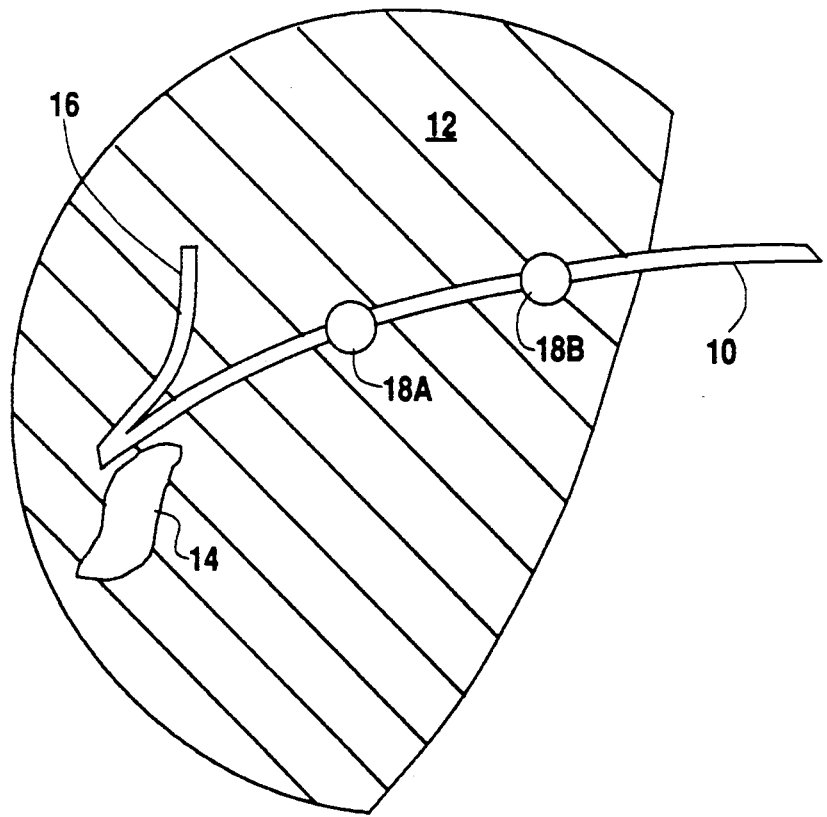
FIG. 2 is a detailed view of section A of FIG. 1 of a preferred embodiment of the present invention positioned in breast tissue having a lesion.
Figure 3:
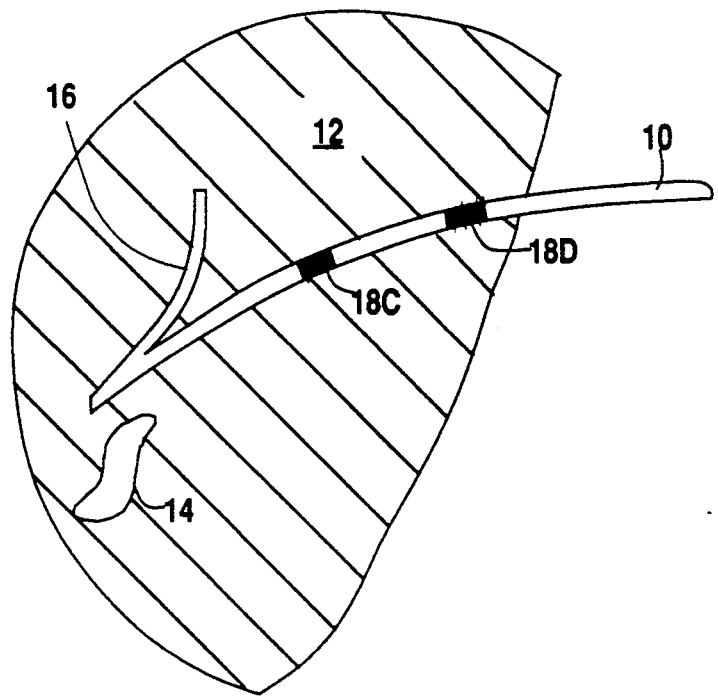
FIG. 3 is a detailed view of section A of FIG. 1 of another preferred embodiment of the present invention positioned in breast tissue having a lesion.

FIG. 1 illustrates modified wire 10 of the present invention only after it has been positioned within tissue 12 by techniques known in the art. Modified wire 10 is secured within the tissue region by a collapsible hook 16 which opens when released from the needle. Hook 16 is collapsed when the wire is contained within the needle. However, when the needle is withdrawn, hook 16 opens and attaches to tissue 12 near lesion 14. Hook 16 is formed by sufficiently bending wire 10 so that it will collapse when placed within the needle. When the needle is withdrawn from tissue 12, the tip of wire 10, corresponding to the bend in the needle, is positioned either near lesion 14 or direotly within lesion 14. FIG. 1, 2 and 3 shows the tip placed near lesion 14, however, the invention clearly allows the tip to be placed directly within lesion 14.

Referring to FIG. 2, a preferred embodiment of modified lesion localization wire 10 having two markers 18A and 18B of the present invention, wherein each marker 18A and 18B having a protrusion extending radially outward from wire 10. Like modified wire 10, markers 18A and ISB are made of radiopaque materials that are detectable when exposed to radiation. Thus, when the tip of wire 10 is being positioned near lesion 14, markers 18A and 18B will also be shown as small protrusions residing along wire 10 a set distance from the tip of the wire and a set distance from lesion 14. Although FIG. 2 illustrates two markers, it is to be appreciated that more than two markers can be used. Also, as few as one marker can be used without deviating from the nature and scope of the invention.

Markers 18A and 18B provide palpable protrusions on wire 10 as shown in FIG. 2. The surgeon is thus, provided with early palpable feedback as to the location of lesion 14 with respect to the marker. When the surgeon makes his incision along the modified wire 10, he will first detect the presence of marker 18B at a relatively shallow depth. If lesion 14 resides near marker 18B, then the surgeon can redirect or veer his incision toward the lesion. Direct-path incision minimizes the amount of unafflicted tissue being severed or removed. Lesion localization wires which do not have markers require that the surgeon cut to the tip of the wire before he can fix the exact location of the shallower lesion. Therefore, conventional, non-marked wires do not provide early feedback needed when lesion 14 reside closer to the markers 18A or 18B than to the tip of wire 10. By having one or more markers on wire 10, there are more target areas or reference points near which lesion 14 can reside. Therefore, the present invention further provides that the wire tip need not be placed immediately adjacent lesion 14. Instead, the tip of wire 10 can be inserted past lesion 14. One or more of the shallower markers 18A and 18B are sufficient as reference points from which the lesion can be located. Because it is no longer necessary that wire tip be placed immediately adjacent lesion 14, fewer repositioning steps are needed to fix wire 10 at the desired location within tissue 12. If a satisfactory position is obtained after only a few attempts, the patient's exposure to radiation is substantially minimized.

Markers 18A and 18B are made of radiopaque material which may include but is not limited to materials such as stainless steel. Moreover, markers 18A and 18B can be either a permanent part of wire 10 or they can be temporarily attached to wire 10. Temporarily attached markers comprise of radiopaque protrusions that can be clamped upon wire 10 at known distances (preferably 1, 2 and/or 3 cm) from the tip of wire 10. The protrusions shown in FIG. 2 extend radially outward from the outer surface of wire 10 so that they become visually detectable, and also, detectable to the surgeon's touch. Marker are spaced along wire 10 such that the spacing between markers is sufficiently greater than the axial length of each marker.

Referring to FIG. 3, an alternative preferred embodiment of modified lesion localization wire 10 is shown having textured markers 18C and 18D. Markers 18C and 18D serve a similar function as markers 18A and 18D by providing palpable feedback to the surgeon during movement of his scalpel along modified wire 10. When the scalpel or the surgeon's fingers touch textured markers 18C or 18D, the surgeon knows the distance along wire 10 to the wire tip. Additionally, the surgeon also knows the exact distance to lesion 14, which may or may not lie near the tip of wire 10. Textured markers 18C and 18D represent areas having textured markings upon wire 10 such that they are either visually detectable or are detectable to the surgeon's touch, or both. The textured markers 18C and 18D extend radially flush with wire 10 and are relatively short in the axial direction when compared to the spacings between markers 18C and 18D or the spacing between 18C and the tip of wire 10.

Figure 4:
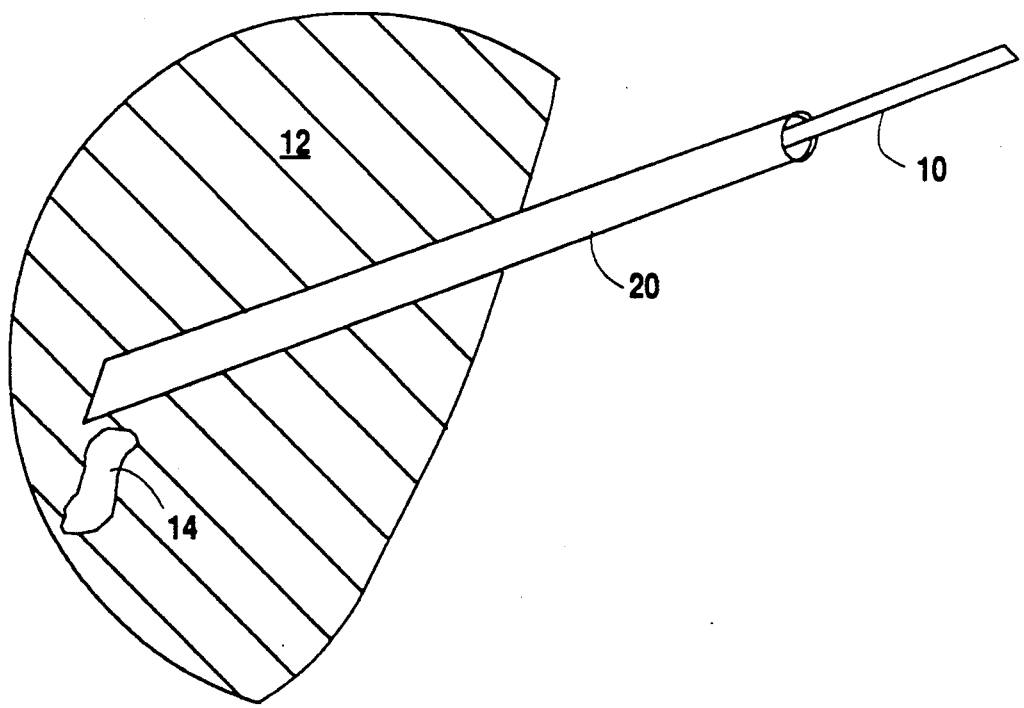
FIG. 4 is a detailed view of section A of FIG. 1 showing a needle for positioning the wire in breast tissue having a lesion.

FIG. 4 illustrates a hollow needle 20 containing wire 10, whereby the distal end of needle 20 and wire 10 are placed into the afflected tissue 12 and positioned as near lession 14 as possible. Needle 20 and wire 10 are guided toward the lesion by taking a series of radiographs or mammographies of the dradiopaque needle 20 and wire 10 which are partially imbedded into the afflected tissue region 12. The tip of needle 20 and wire 10 can be repositioned nearer lesion 14 after each X-ray. With needle 20 at the final desired position, wire 10 can be released from the needle encasement such that the tip or wire 10 becomes securd tothe tissue 12 at the sample point at which the tip of the needle previously resided. With the wire 10 firmly secured in place, needle 20 can then be withdrawn from tissue 12 thereby leaving only the wire 10 partially imbedded into the tissue 12.

The foregoing description of the invention has been directed to a particular preferred and alternative embodiment of the present invention. It will be apparent, however, to those skilled in the art that modifications and changes in both apparatus and method may be made without departing from the scope and spirit of the invention. For example, instead of using two markers, any number of markers may be used. It is preferred that if more than one marker is used, the markers be spaced apart greater than the axial length of each marker, and that each marker's axial length is somewhat short (i.e., generally less than 0.5 cm). Also, the spacings between markers can be varied considerably depending upon the surgeon's preference. Additionally, the markers can be of any substance suitable in a tissue environment that embodies a palpable surface and that surface need not be limited to radially extended protrusions or to textured areas shown in FIGS. 1 and 2, respectively, but includes any palpable surface of which is either detectable by the surgeon's senses (e.g., either sight, sound, or touch). Therefore, it is the applicant's intention in the following claims to cover all such equivalent modifications and variations which fall within the true spirit and scope of the invention.

I claim:

1. A device for localizing a lesion area within a breast, comprising:
   a hollow needle with one end insertable into or near said brest lesion area;
   a flexible, radiopaque wire having a distal end placed within said hollow needle;

a collapsible hook formed at the distal end of said wire by bending said wire at least 90 degrees, said collapsible hook having a tip formed at the bend in said wire, wherein said tip is insertable into or near said lesion area; and, at least two radiopaque, palpable markers configured upon said wire and spaced a known distance from said tip, each said marker is generally less than 0.5 cm in axial length and is recognizable tothe touch as being a known distance fromthe tip of said wire such that the spacing between said markers and the spacing betweens aid tip and said marker nearest said collapsible hook is substantially greater than the axial length of each said marker.

2. A device for localizing a lesion area within a breast, comprising:

a hollow needle with one end insertable into or near said breast lesion area;

a flexible, radiopaque wire having a distal end placed within said hollow needle;

a collapsible hook formed at the distal end of said wire by bending said wire at least 90 degrees, said colapsible hook having a tip formed at the bend in said wire, wherein said tip is insertable into or near said lesion area; and, at least two radiopaque, palpable markers configured upon said wire and paced a known distance from said tip, each said marker is generally less than 0.5 cm in axial length and is recognizable as being ak nown distance from the tip of said wire such that the spacing between said markers and the spacing between said tip and said marker nearest said collapsible hook is substantially greater than the axial length of each said marker, said markers are protrusions extending radially outward from said wire wherein each of said protrusions extend longitudinally a short distance along said wire such that each of said markers are attachable to said wire and of larger diameter than said wire.

3. A method for locating a lesion in breast tissue, comprising the steps of:

inserting a needle containg a wire having at least two distnct and separate markers into said breast tissue;

positioning the end of said needle within or near said lesion by moving said needle according to a radiograph display;

withdrawing the needle leaving the end of the wire secured within or near said lesio and one of said at least two markers positioned a known distance from said lesion;

inserting a scalpel into said brest tissue along said wire; and, palpably locating one of said at least two markers and determining a depth in which to insert said scalpel substantially near said lesion in accordance with said known distance between said located marker and said lesion.

4. A device for localization of a lesion in tissue, comprising:

a wire having a collapsible hook formed at one end of said wire and at least two protursions extending radially outward from said wire and each protrusion being generally less than 0.5 cm in axial length and spaced a known distance form said collapsible hook along said wire such that the spacing between said protrusions and the spacing between said tip and said protrusion nearest said collapsible hook is substantially greater than the axial length of each said protrusion; and said hook being insertable into the tissue to a point near said lesion.

* * * * *

UNITED STATES PATENT AND TRADEMARK OFFICE
CERTIFICATE OF CORRECTION

PATENT NO. : 5,158,084                                   Page 1 of 2
DATED      : October 27, 1992
INVENTOR(S): Abraham A. Ghiatas It is certified that error appears in the above-indentified patent and that said Letters Patent is hereby corrected as shown below:

In claim 1 at column 7, line 9, insert a space between "to the".

In claim 1 at column 7, line 10, insert a space between "from the".

In claim 1 at column 7, line 12, change "betweens" to --between--.

In claim 1 at column 7, line 12, change "aid" to --said--.

In claim 2 at column 7, line 23, change "colapsible" to --collapsible--.

In claim 2 at column 7, line 27, change "paced" to --spaced--.

In claim 2 at column 7, line 29, change "ak" to --a--.

In claim 2 at column 7, line 30, change "nown" to --known--.

In claim 3 at column 8, line 6, change "containg" to --containing--.

In claim 3 at column 8, line 7, change "distnct" to --distinct--.

In claim 3 at column 8, line 12, change "lesio" to --lesion--.

In claim 3 at column 8, line 15, change "brest" to --breast--.

UNITED STATES PATENT AND TRADEMARK OFFICE
CERTIFICATE OF CORRECTION

PATENT NO. : 5,158,084

DATED : October 27, 1992

INVENTOR(S) : Abraham A. Ghiatas

It is certified that error appears in the above-indentified patent and that said Letters Patent is hereby corrected as shown below:

In claim 4 at column 8, line 25, change "protursions" to --protrusions--.

In claim 4 at column 8, line 28, change "form" to --from--.

Signed and Sealed this

Fifth Day of October, 1993

Attest:

BRUCE LEHMAN

Attesting Officer     Commissioner of Patents and Trademarks